United States Patent [19]

Brierley

[11] Patent Number: 5,106,196

[45] Date of Patent: Apr. 21, 1992

[54] SINGLE ADJUSTMENT SPECULAR REFLECTION ACCESSORY FOR SPECTROSCOPY

[76] Inventor: Philip R. Brierley, 2605 McKenna Blvd., Madison, Wis. 53711

[21] Appl. No.: 570,478

[22] Filed: Aug. 21, 1990

[51] Int. Cl.$^5$ ............................................. G01N 21/55
[52] U.S. Cl. ...................................... 356/445; 356/346
[58] Field of Search ................................ 356/445–448, 356/244, 346, 128, 135, 136, 237, 300

[56] References Cited

U.S. PATENT DOCUMENTS

| | | | |
|---|---|---|---|
| 3,240,111 | 3/1966 | Sherman et al. | 6/ |
| 3,420,138 | 1/1969 | Hansen . | |
| 3,491,366 | 1/1970 | Harrick . | |
| 4,640,617 | 2/1987 | Hughes et al. | 356/244 |
| 4,730,882 | 3/1988 | Messerschmidt . | |
| 4,812,041 | 3/1989 | Doyle | 356/346 |
| 4,966,457 | 10/1990 | Hayano et al. | 356/237 |

Primary Examiner—F. L. Evans
Assistant Examiner—K. P. Hantis
Attorney, Agent, or Firm—Quarles & Brady

[57] ABSTRACT

A specular reflection analyzer uses opposed parabolic mirror sections to direct a focussed beam at an angle of incidence against a sample surface and to receive a reflected beam at a corresponding angle of reflection. A first collimated beam of light is directed at a constant angle against the first parabolic mirror from a beam diverter movable parallel to the mirror's axis of symmetry and within the first collimated beam of light. Translation of the constant angle beam along a meridian on the surface of the first parabolic mirror changes the angle of incidence of a beam focused on the sample without changing the focal point. The light reflected from the sample is received in a corresponding manner by the second parabolic mirror and transformed into a collimated beam of constant angle to be received by a second beam diverter tracking the first beam diverter. Transfer optics may be used to adapt the apparatus for use in a conventional transmission spectrometer.

11 Claims, 4 Drawing Sheets

SINGLE ADJUSTMENT SPECULAR REFLECTION ACCESSORY FOR SPECTROSCOPY

BACKGROUND OF THE INVENTION

1. Field of the Invention The field of the invention is Fourier transform infrared spectroscopy and in particular accessories for making specular reflection analysis with such spectrometers.

2. Background Art

Fourier transform infrared spectroscopy (or FTIR) is a technique for studying the composition of matter by measuring the characteristic absorption of specific wavelengths of infrared radiation by the matter. The absorption may be measured with either transmitted or reflected radiation.

In transmission spectroscopy, a beam of infrared radiation of known and time-variant spectral composition is passed through an at least partially transmissive sample. The resulting transmission absorption spectrum is then compared to standard transmission absorption spectra to identify the spectral adsorption characteristics of the sample to permit identification of the sample's constituents.

With opaque samples, the technique of specular reflection spectroscopy may be used. In reflection spectroscopy, a beam of infrared radiation of known spectral and time variant composition is directed against the surface of a planar sample at a predetermined angle of incidence. The spectrum of the energy reflected at an opposing reflection angle, equal in magnitude to the incidence angle, is then measured. As with transmission spectroscopy, the resulting reflection absorption spectrum may be compared to known reflection absorption spectra to reveal information about the composition of the surface or the coating of the surface of the sample.

The spectrum of the reflected beam may also be used to reveal information about the physical structure of the sample, for example, the thickness of a thin film applied to an opaque or reflective substrate. Multiple reflections of the incident radiation in the thin film can cause optical interference effects which sinusoidally modulate the intensity of the measured reflection absorption spectrum as a function of frequency. The "frequency" of this modulation is dependent on the thickness and the refractive index of the film and the angle of incidence of the impinging radiation.

If the angle of incidence of the impinging radiation and the refractive index of the film are known, the thickness of the film may be deduced from the modulation frequency.

If the thickness of the film is such that the resulting reflection spectrum exhibits less than one cycle of modulation across the spectral range of the measurement, the resulting accuracy of the measurement of the film thickness may be poor. Varying the angle of incidence (and reflection) of the incident beam may be used to increase the modulation of the spectrum and hence improve the accuracy of the measurement. Accordingly, the ability to adjust the angle of incidence of the incident radiation is desirable to allow a wide range of film thickness to be evaluated. With very thin films on metallic substrates, the incident radiation beam also may be polarized and adjusted to strike the sample at a high angle of incidence. This further increases the intensity of the spectral features of the reflected beam. The optimum angle for this measurement has been calculated by R. G. Greenler, *J. Chem. Physics* 44, 10 (1966) and is approximately 88°. The ability to accurately adjust the angle of incidence of a polarized incident beam to 88° may increase the intensity of the spectral features by up to two orders of magnitude.

Standard spectroscopy instruments are conventionally designed for transmissive rather than reflective spectroscopy. For this reason, the spectroscopic light source, the sample chamber, and the detector are ordinarily arranged along a straight path (the "spectroscopic axis"). In a center focus instrument, the beam from the light source ("source beam") is focussed at a focal point centered within the sample chamber. A diverging beam ("detector beam") exits the sample chamber from the focal point and is collected by the detector for analysis. Reflective spectroscopy may be performed with such standard spectroscopic equipment by inserting a specially designed accessory within the sample chamber that will intercept the source beam, divert it to the sample for reflection, and return it after reflection to the detector.

Figure 1A:
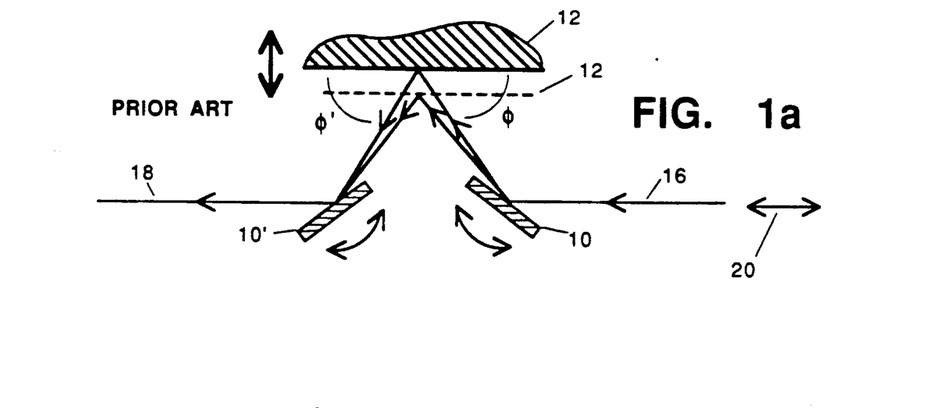
FIG. 1(a) is a cross-sectional view of a first background art specular reflection accessory viewed at an angle perpendicular to the spectroscope axis and showing the multiple adjustments required.

In one design for a prior art specular reflection accessory, as shown in FIG. 1(a), a first transfer mirror 10 reflects the source beam 16 toward a sample 12 removed from the spectroscopic axis 70, at a given angle of incidence $\phi$. A second transfer mirror 10' receives the reflected light from the sample 12 at a reflection angle $\phi'$, of equal magnitude to the incidence angle $\phi$, and reflects the received light back to the detector. The drawback to this system is that when the accessory is placed in the spectrometer, an extra path length is introduced causing a subsequent defocussing of the detector beam and the loss of signal. The path length of the beam with the accessory inserted is equal to the distance from the transfer mirror 10 to the sample 12 to the second transfer mirror 10' while the distance with the accessory removed is equal to the distance from the transfer mirror 10 to the transfer mirror 10'. This accessory is thus a simple low performance device which is designed to be used at a fixed angle of incidence to the sample.

Figure 1B:
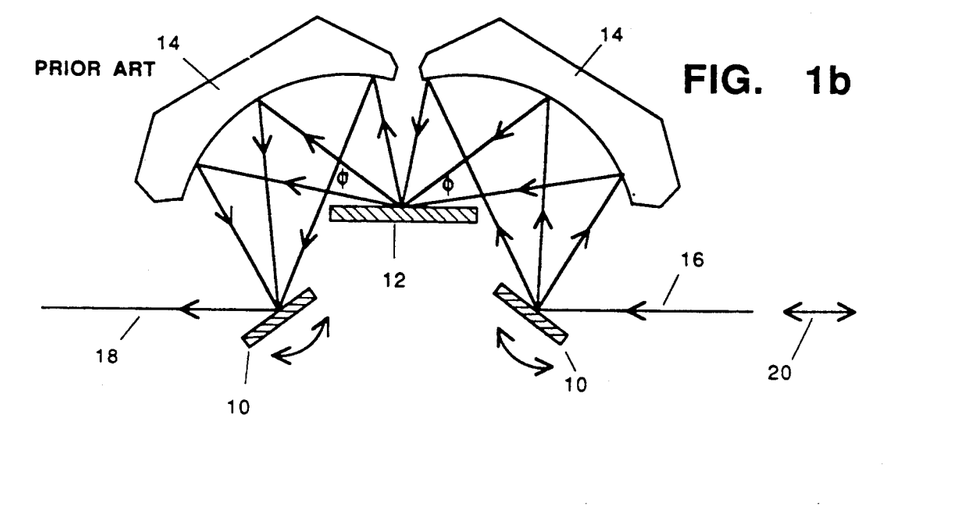
FIG. 1(b) is a cross-sectional view of a second background art specular reflection accessory having two adjustments and showing the restricted sample size demanded by the folded optical path.

A second design for a prior art specular reflection accessory is shown in FIG. 1(b). A first transfer mirror 10 directs the source beam 16 away from the spectroscope axis 70 towards a first ellipsoidal mirror 14 which reflects the beam back toward the spectroscope axis 70 and the sample 12. The ellipsoidal mirror has a first focal point at the first transfer mirror 10 and a second focal point on the surface of the sample 12 and hence with rotation of the first transfer mirror 10, the source beam 16 remains directed to the sample 12 by the ellipsoidal mirror 14 with only the angle of incidence $\phi$ changed. A corresponding second ellipsoidal mirror 14' and second transfer mirror 10' collect the reflected light and return it to the detector for analysis. The two transfer mirrors 10 and 10' must be realigned to change the angles of incidence and reflection while the sample 12 remains stationary. The drawbacks of this design are that the two mirrors must move in precise unison, and that the sample 12 is fixed inside of the instrument which is both inconvenient and limiting as to the size of the sample.

Figure 1C:
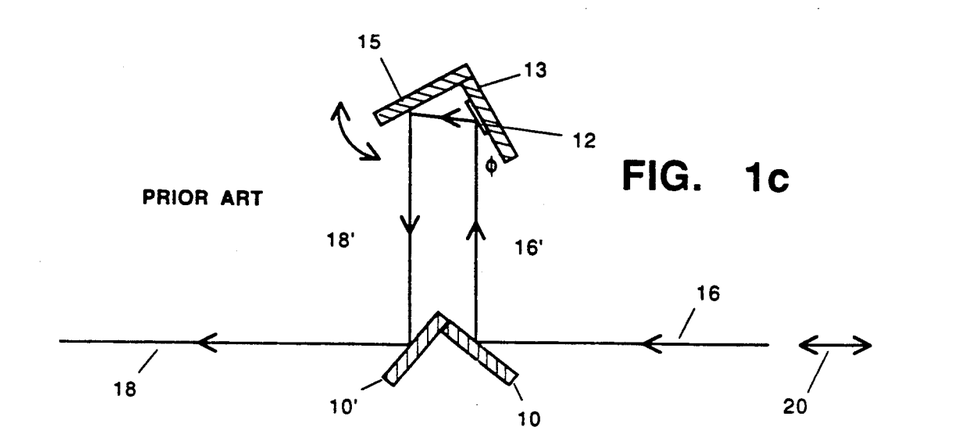
FIG. 1(c) is a cross-sectional view of a third background art specular reflection accessory having only one adjustment but requiring rotation of the sample on a compact sample holder.

A third design for a specular reflection accessory, shown in FIG. 1(c), uses a rotatable sample holder 13 joined at a right angle to a sample mirror 15. A first transfer mirror 10 directs the source beam 16 along a deflection path 16' toward the sample 12 which is displaced away from the spectroscope axis 70. The reflected beam 18' from sample 12 is in turn reflected by the sample mirror 15 along a return path 18' toward the spectroscope axis 70. As before, the second transfer mirror 10' directs the reflected beam to the detector for analysis. As a result of the geometry of the sample holder 13 and sample mirror 15, the reflected beam from 18' the sample 12 is parallel to the deflection path 16'. This parallelism of the return path 18' with the deflection path 16' is independent of the angle of the sample 12 with respect to the deflection path 16'. Hence the angle of incidence $\phi$ and reflection $\phi'$ may be changed by rotating the sample holder 13 without adjusting the transfer mirrors 10 and 10'. The drawbacks to this design are the limitation of the size of sample 12 imposed by sample holder 13, and the need to clamp the sample 12 against the sample holder 13 to hold it during rotation.

SUMMARY OF THE INVENTION

In the present invention, two parabolic mirrors, and two joined beam diverters movable along a beam axis, are employed to vary the angle of incidence and reflectance of a beam focussed on a sample with a single linear adjustment and without changing the location of the sample's surface.

Specifically, input transfer optics receive a source beam from a spectrometer and direct it as a collimated input beam along a beam axis. An input diverter mirror reflects the input beam at a constant angle toward an input parabolic mirror which focuses the beam on a sample at a incident projection angle.

Reflected light from the sample is received at a reflection or detection angle by an output parabolic mirror and directed as a constant angle output beam to an output diverter mirror. The output diverter mirror reflects the beam along the beam axis to output optics which produce a detector beam for return to the spectroscope.

The input and output diverter mirrors are movable along the beam axis and joined so that the angle of projection of the input parabolic mirror equals the angle of detection of the output parabolic mirror throughout the range of movement of the diverter mirrors along the beam axis.

It is one object of the invention to produce a specular reflection accessory which may be readily incorporated into a conventional FTIR spectroscopy instrument and which does not unduly limit the size of the sample. The use of opposed parabolic mirrors permits the displacement of the sample to a position outside of the volume of the optical assembly. Accordingly, sample sizes are not restricted by their possible interference with the optical path.

It is another object of the invention to provide a means of projecting and detecting light in a specular reflectance system requiring only simple linear movement of a single optical component. The angle of projection is determined by the position of the input diverter mirror along the beam axis and hence the area along a meridian of the parabolic mirror that is exposed. Correspondingly, the angle of detection is determined by the position of the output diverter mirror along the beam axis. The input and output diverter mirrors are joined to ensure that the angle of projection equals the angle of detection as is required for specular reflection measurements and to permit equal adjustment of both angles with simple linear movement of the joined mirrors.

It is another object of the invention to permit adjustment of the angle of projection and detection of a specularly reflected light beam without affecting the focal point of the beam. The focal point of the input and output parabolic mirrors is determined by the angle of the input and output diverter mirrors with respect to the beam axis. This angle is held constant when the diverter mirrors move along the beam axis and hence the focal point remains fixed as the angle of projection and detection are changed.

In one embodiment of the invention, an ATR crystal is placed to receive light from the input parabolic mirror at a projection angle. Light transmitted by the crystal is received by the output parabolic mirror at an angle of detection equal to the angle of projection. The beam of light entering the ATR crystal (attenuated total reflectance) experiences a series of internal reflections dependant in number and quality on the angle of projection. At each reflection, along the face of the ATR crystal having an interface with the sample, absorption into the sample occurs. Varying the angle of projection and detection changes the character and degree of the absorption.

It is thus another object of the invention to provide the benefits of simple adjustment of projection and detection angles to attenuated total reflectance measurements.

Other objects and advantages besides those discussed above shall be apparent to those experienced in the art from the description of a preferred embodiment of the invention which follows. In the description, reference is made to the accompanying drawings, which form a part hereof, and which illustrate two examples of the invention. Such examples, however, are not exhaustive of the various alternative forms of the invention, and therefore reference is made to the claims which follow the description for determining the scope of the invention.

DETAILED DESCRIPTION OF THE PREFERRED EMBODIMENT

Figure 2:
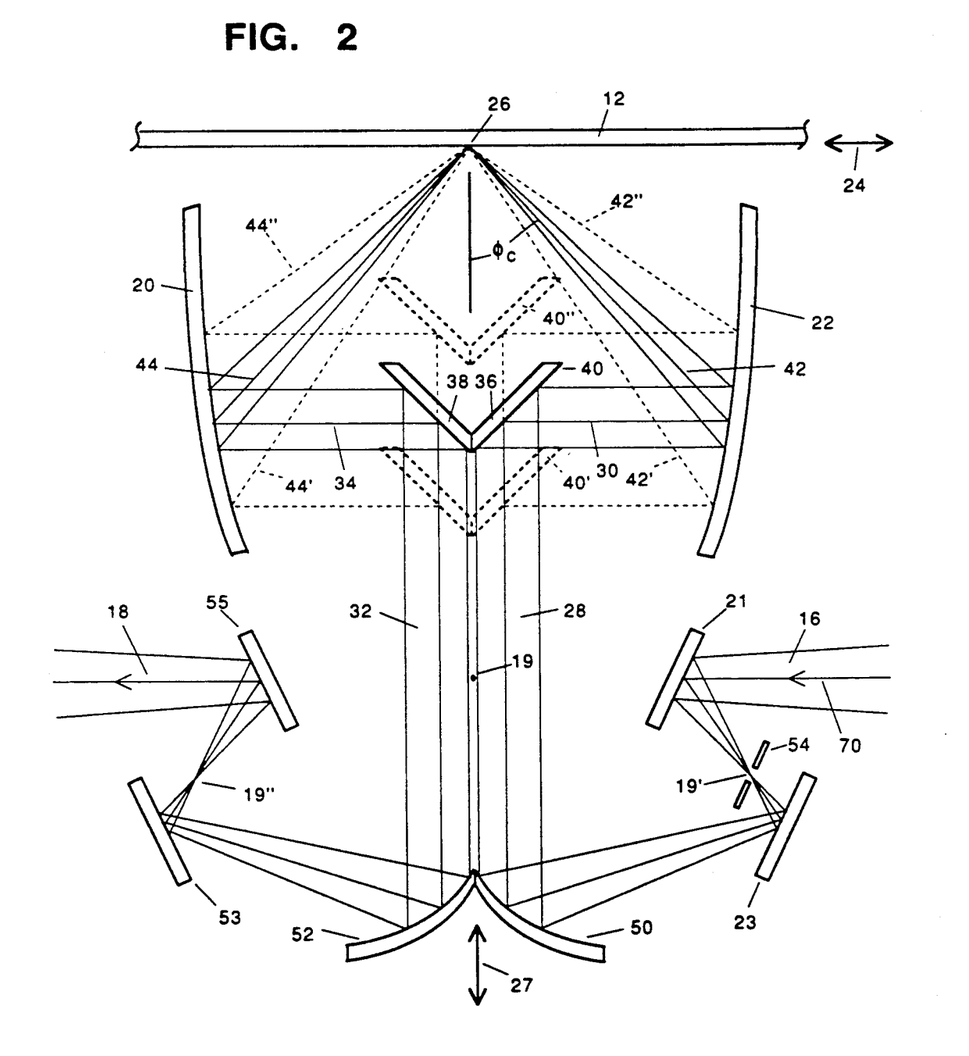
FIG. 2 is a cross-sectional view taken along the plane of the spectroscope axis showing the specular reflection accessory of the present invention with coincident parabolic mirror and beam axes.

Shown in FIG. 2 is a diagram of the optical path of a specular reflector accessory for an FTIR instrument constructed in accordance with the present invention. It is to be understood that the complete assembly of the optical elements illustrated in FIG. 2 can be assembled within a casing sized and shaped so that it may be inserted into the sample chamber of an otherwise conventional FTIR instrument. In such an instrument, the time variant infrared beam is directed along an optical axis to a focus in the sample chamber. The accessory of FIG. 2 is intended to be inserted in that chamber to alter the optical path of the infrared light beam, to allow the measurement of the specular reflectance characteristics of a sample.

Referring to FIG. 2, a source beam 16 of infrared radiation is produced by a laser and interferometer (not shown), which are normal components of Fourier Transform Infrared Spectroscopy ("FTIR") instruments, as is generally known in the art. The source beam 16 is directed along lateral spectrometer optical axis 70 and converges on a focal point at 19. The virtual focal point 19 is intended normally to be the locus of the sample to be analyzed. In the arrangement of FIG. 2, the source beam is reflected first by path folding mirror 21 and then by path folding mirror 23, which together cause the source beam 16 to double back upon itself before being directed along a new path parallel to, but displaced vertically downward below, the spectrometer axis 70. As a result of the path folding mirrors 21 and 23, the true focal point 19' of source beam 16 is now between path folding mirrors 21 and 23. Hence the displaced beam exiting the path folding mirrors 21 and 23 is a diverging beam. An iris 54 is placed around this actual focus 19', and may be adjusted in aperture to control the area of the sample 12 that will be illuminated, as described below, and thus permits the apparatus to be used with an arbitrarily small sample 12.

The diverging beam from path folding mirror 23 is collimated by a fixed parabolic mirror 50 to form a fixed, generally vertical, collimated beam 28 along a new, vertical beam axis 27. The path folding mirrors 21 and 23, together with the parabolic mirror 50, function as transfer optics to allow the specular reflection accessory of the present invention to fit within the sample chamber of a conventional transmission spectrometer. The transfer optics thus convert the horizontal focussing light beam to a vertical collimated light beam.

A planar, input diverter mirror 36 is carried on vertically adjustable precision guideways, of any type well known to the art, to provide for accurate linear motion of the diverter mirror 36, without rotation, along the vertical path of the collimated beam 28. The diverter mirror 36 intercepts the collimated beam 28 and reflects it at 90° to produce a collimated, horizontal, constant angle beam 30.

The constant angle beam 30 is directed to the concave reflecting surface of an input parabolic mirror 22. The parabolic mirror 22 has a surface formed into a section of a parabola having its axis of symmetry 24 parallel to the collimated beam 30. Depending on the position of the diverter mirror 36, the constant angle beam 30 strikes the surface of parabolic mirror 22 at various areas along a meridian defined with respect to its axis of symmetry 24.

An inherent property of parabolic mirrors is that they focus beams of parallel light to a single, fixed focal point. Thus the angle at which any set of light rays reflected in such a mirror approaches the focal point varies depending on where along the parabolic shape the rays strike the mirror's surface. The parabolic mirror 22 in FIG. 2 is orientated and positioned so as to focus the collimated rays of the constant angle beam 30 into a converging beam 42 directed at a focal point 26 upon a sample 12. The angle of incidence by which the light rays of the converging beam 42 approaches the focal point 26 is determined by the location on the parabolic shape of the parabolic mirror 22 toward which the constant angle beam 30 is directed by the input diverter mirror 36. When the diverter mirror 36 is in the position 40 illustrated in FIG. 2, approximately centered within the vertical range of movement of the diverter mirror 36, the converging beam 42 from the parabolic mirror 22 is directed at the focal point 26 along a median oblique angle to strike the sample 12 at angle of incidence designated $\phi_c$. When the diverter mirror 36 is moved along linearly to position 40', away from the sample 12 and the focal point 26, a converging beam 42' is directed at the focal point 26 at a more shallow angle, to strike the sample 12 at an angle of incidence less than $\phi_c$. Conversely, when the diverter mirror 36 is moved upwardly linearly to a position 40", closer to the sample 12 and the focal point 26, a converging beam 42" is directed at the focal point 26 at a greater angle, to strike the sample 12 at an angle of incidence greater than $\phi_c$.

Accordingly, simple linear motion of the input diverter mirror 36 serves to alter or adjust the angle of incidence of the converging beam 42 onto the sample 12, without changing the focal point 26. The angle of incidence will also be termed here the angle of projection.

It will be recognized that changes in the section of the parabolic mirror 22 onto which the constant angle beam 30 is directed by movement of the diverter mirror 36 is preferably along a single meridian of the parabolic mirror 22 running in a plane perpendicular to that of the sample surface 12. This provides the advantages of a simple relationship between the movement of the diverter mirror 36 and the angle of incidence $\phi$, and restricts the centerpoint of the beam 42 impinging on the sample 12 to a single plane. Nevertheless, considerable vertical variation in the area of exposure of the constant angle beam 30 on the surface of the parabolic mirror 22 may be readily tolerated, and the motion of the exposed area on the parabolic mirror 22 need only have a component of motion in the direction perpendicular to the surface of sample 12. Henceforth movement along the meridian will be understood to means movement which has a component perpendicular to the surface of sample 12.

It should be noted that the focal point 26 may be displaced beyond the edges of the parabolic mirror 22, and hence both large and small sizes for the sample 12 may be readily accommodated, without interfering with the optical path between the diverter mirror 36 and the parabolic mirror 22.

The diverging beam of reflected radiation 44 from the sample 12 is collected by a second parabolic mirror 20 located symmetrically opposing the first parabolic mirror 22 about the axis of symmetry 24. The second parabolic mirror 20 collimates the diverging beam of the reflected light 44 from the sample 12 into a generally horizontal constant angle beam 34. These relationships are generally the reverse of the relationships between the constant angle beam 30 and the parabolic mirror 22.

The constant angle beam 34 is reflected from a specific area along a meridian of the parabolic mirror 20 determined by the angle of reflectance of the reflected beam 44. The second diverter mirror 38 is positioned to deflect the collimated constant angle beam 34. Since the parabolic mirrors 20 and 22 are complementary, as are the diverted mirrors 36 and 38, for light reflected in the reflected light beam 44 at an angle equal to the angle at which the incident light beam 42 hits the sample, the light beam 44 would be directed horizontally off the parabolic mirror 20 to the diverter mirror 38 where the light beam would be directed vertically downward as a second collimated beam 32. The position of the diverter mirror 38 along the beam axis 27 determines the angle at which the second parabolic mirror 20 is maximally sensitive to light from the sample 12. This angle will be termed the detection angle, and in specular reflection spectroscopy is normally equal to the angle of reflectance.

Thus the constant angle beam 34 is received by the second diverter mirror 38 which is joined to and is symmetrical with the first diverter mirror 36 about axis of symmetry 24. This symmetry, in addition to the symmetry of the parabolic mirrors 20 and 22, ensures that the angle of projection of the incident light ray 42 will equal the angle of detection of the reflected light ray 44.

The second diverter mirror 38 diverts the constant angle beam 34 into the second collimated beam 32 directed generally vertically downward and parallel to the collimated beam 28 along beam axis 27. Transfer optics including a pair of beam folding mirrors 55 and 53 and a parabolic mirror 52, symmetrically opposed about axis 24 to the beam folding mirrors 21 and 23 and the parabolic mirror 50, as described above, convert the collimated beam 32 into a divergent detector beam 18 aligned with the spectroscope axis 70, and aligned with the source beam 16 to share the virtual focus 19. Specifically, the collimated beam 32 is focused by the parabolic mirror 52 and directed into a converging beam to the path folding planar mirror 53 which together with the path folding planar mirror 55 produces the detector beam 18, as described above. The actual focal point 19" of the detector beam 18 is between the path folding mirrors 53 and 50. Hence the detector beam 18 is diverging as it exits the path folding mirrors 55 and 53. As is understood in the art, the detector beam 18 is received by a detector on the spectroscopic instrument (not shown) for spectral analysis. The detector beam would thus be a diverging beam optically similar to the beam exiting from a conventional sample chamber. Thus, no modifications need to be made to the spectroscopic instrument to accommodate the accessory of the present invention.

Figure 3:
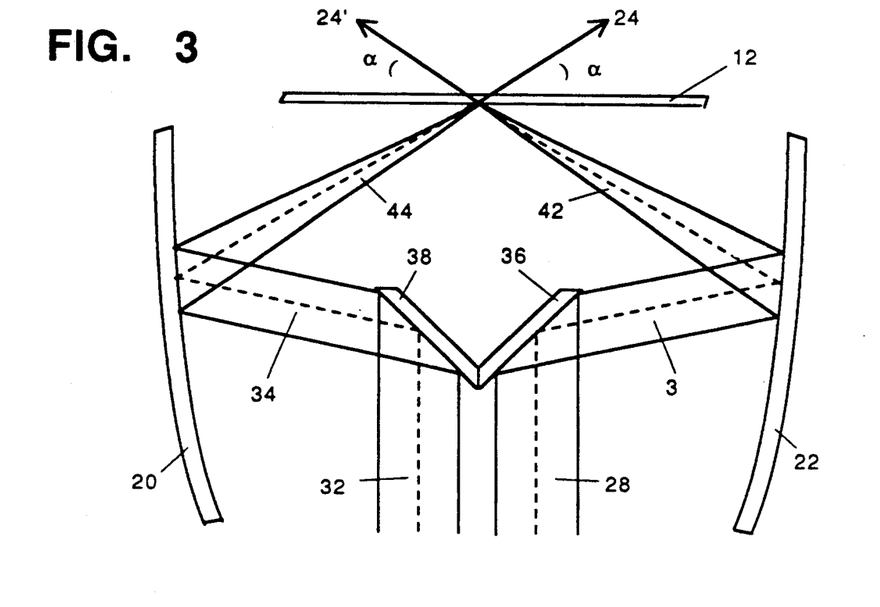
FIG. 3 is a detail of a cross-section of the specular reflection accessory of the present invention similar to that of FIG. 2 showing an embodiment with divergent parabolic mirror and beam axes.

In the embodiment described above, the parabolic mirrors 22 and 20 share a common axis 24 with each other. In a second embodiment, as shown in FIG. 3, the mirrors 22 and 20 are canted inwardly at their edges nearest the sample 12 so that mirror 22 has axis of symmetry 24 and mirror 20 has axis of symmetry 24', which axes are divergent equally about the axis 27 parallel to the surface of the sample 12. The angles of the diverter mirrors 36 and 38 with respect to collimated beams 28 and 32 are accordingly adjusted to follow this canting of the parabolic mirrors, and to direct the constant angle collimated beams 30 and 34 at an angle perpendicular to the axis of symmetry 24 or 24' of the respective parabolic mirror 20 and 22. Thus if the axes of symmetry 24 and 24' of the parabolic mirrors 20 and 22 are tipped by angle $\alpha$, the corresponding diverter mirrors 38 and 36 are tipped by the angle $\alpha/2$ to preserve the relationship between the angle of the constant angle beams 30 and 34 and the axis of symmetry of the respective mirror.

This canting of the parabolic mirrors 20 and 22 permits a higher range of angles of incidence and reflection to be achieved with the same motion of the diverter mirrors 36 and 38. Conversely, as will be apparent from this description, the parabolic mirrors 20 and 22 and the diverter mirrors 36 and 38 may be tipped in the opposite direction to permit a lower range of angles of incidence and reflection to be achieved with the same motion of the diverter mirrors 36 and 38.

Figure 4:
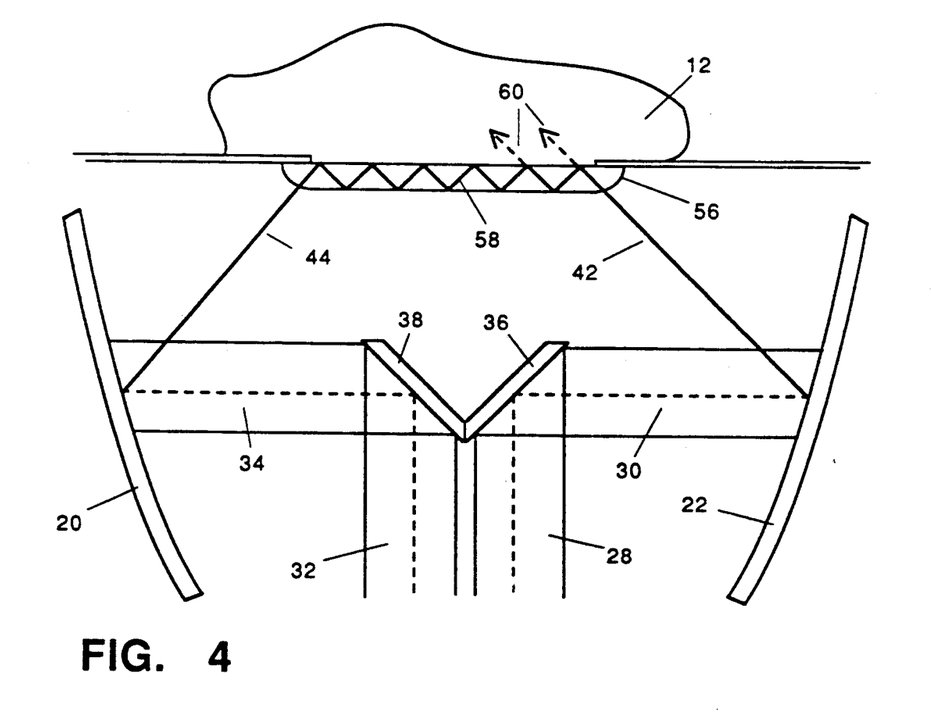
FIG. 4 is a detail of a cross-section the specular reflection accessory of the present invention similar to that of FIG. 2 showing the use of an internal reflection crystal in conjunction with the sample.

Referring now to FIG. 4, in one embodiment, the upper face of an crystal 56 for attenuated total reflectance ("ATR") measurements may been placed against sample 12. Such crystals 12 are known in the art and are useful for measuring the spectral characteristics of soilds, gaseous, or liquid samples. The converging beam 42 is focussed at and enters one end of the crystal 56 and experiences multiple reflections 58 against the upper and lower face of the crystal 56 as it traverses the length of the crystal in a saw tooth pattern. At each point of internal reflection against the upper face of the crystal in contact with sample 12, some light 60 is absorbed by the sample 12. The amount of the absorbed radiation 60 is dependant on the total number of internal reflections, the angle of those reflections, and the relative properties of the crystal 56 and the sample 12. Movement of the diverter mirror 36 and 38 changes the angle at which beam 42 enters the crystal 56, and thus changes the number and angle of the internal reflections.

The planar mirrors 21, 23, 36, 38, 53, and 55 described above are manufactured from optical flats with a first surface coating of an infrared reflecting material such as gold or aluminum. The parabolic mirrors 20 and 22 are constructed from an electro-formed or diamond turned parabolic mirror polished and cut into sections.

The advantage of the accessory of the present invention is that variations in the angle of specular reflection measurements of a sample can be made with only a single linear adjustment. By adjusting the vertical position of the diverter mirrors 36 and 38, which are joined so that they move as a unit, the angle of incidence of light impinging on the sample is adjusted. Since the output optics are complementary to the input optics, and since the diverted mirrors 36 and 38 are joined in movement, it is inherent in this simple linear movement that reflected light is always captured and properly reflected out of the accessory. Since only a single linear movement is needed, there are no problems of alignment and there is not the mechanical complexity of causing two optical surfaces to move coordinately, thus making the device simpler to operated and inherently more reliable. The provision for the iris 54 allows the size of the beam to be adjusted so that the beam can be reduced in size for small samples without loss of any of the other advantages of the accessory. All these features have been accomplished in a unit which can still fit within the sample chamber of a conventional FTIR instrument with otherwise conventional optics.

Figure 5:
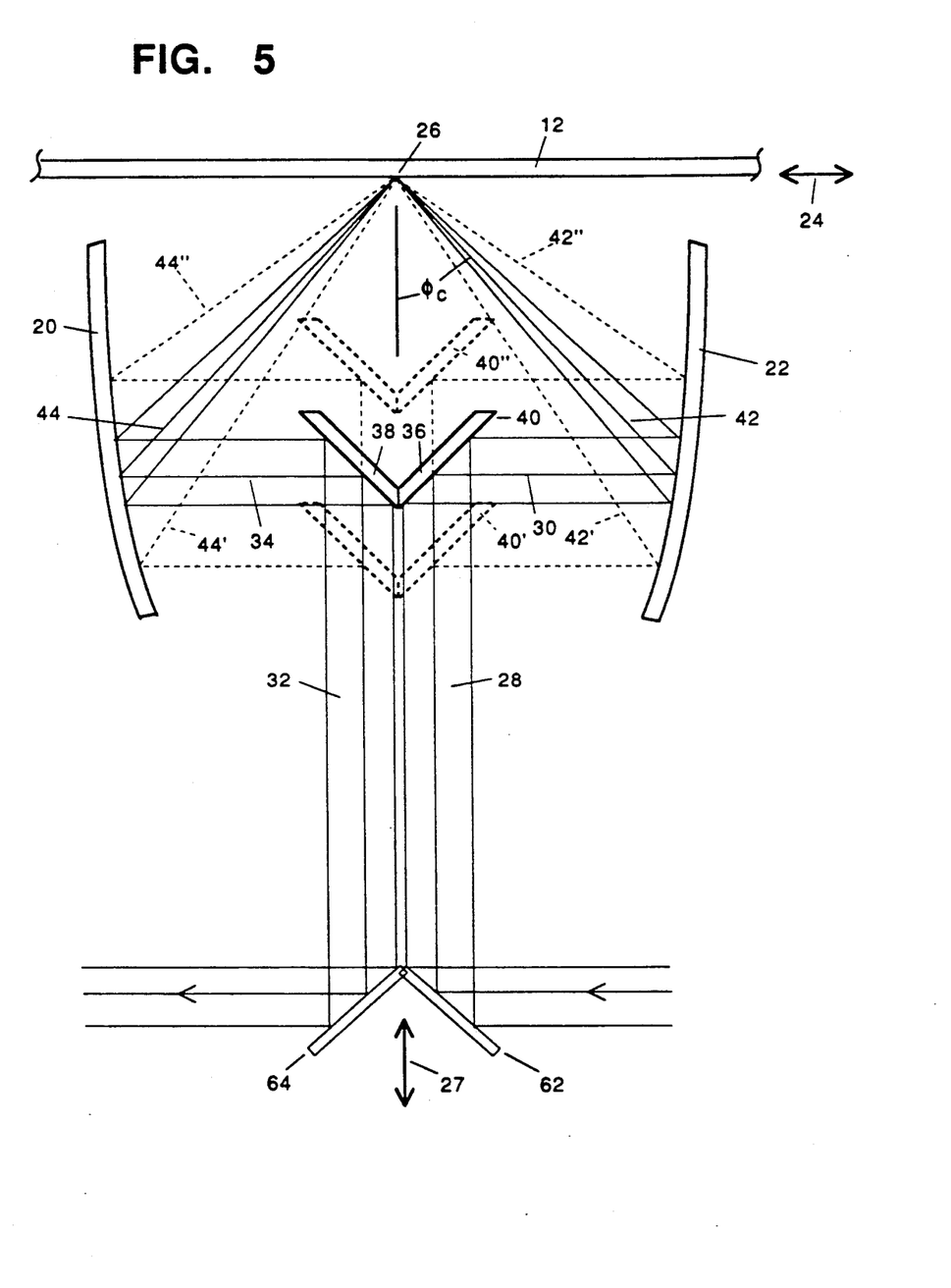
FIG. 5 is a cross-sectional view taken along the plane of the spectroscope axis of an alternative embodiment of the present invention.

Shown in FIG. 5 is another variation on an accessory in accordance with the present invention. The embodiment of FIG. 5 is intended for use with spectrometers which have an external collimated beam port. In the embodiment of FIG. 5, the input transfer optics of mirrors 21, 23 and 50 of FIG. 2 have been replaced by a single input transfer mirror 62, which directs the input collimated beam upward to form the collimated input beam 30. Similarly, on the output side, the output transfer optics of the mirrors 52, 53, and 55 of FIG. 2 have been replaced by a single output transfer mirror 64 to divert the output collimated beam 32 horizontally out of the accessory. In this variation, since the input and the output beams are collimated, any detector assembly would likely include focussing mirrors. This variation is most likely to be used outside of an instrument rather than in the sample chamber of an instrument, and thus has the advantage that the sample chamber remains free for uses other than variable specular reflectance measurement. Other variations in transfer optics, including converging input and collimated output, or vice versa, are also possible.

The above description has been that of a preferred embodiment of the present invention. It will occur to those who practice the art that many modifications may be made without departing from the spirit and scope of the invention. For example, spherical mirrors may be substituted for the parabolic mirrors for less demanding applications or for high angles of incidence and reflectance. In order to apprise the public of the various embodiments that may fall within the scope of the invention, the following claims are made.

I claim:

1. A specular reflection system for measuring the specular reflection from a sample comprising:
   input transfer optics for receiving a source beam and directing a collimating input beam along a beam axis;
   output transfer optics for receiving a collimated output beam directed along the beam axis to produce a detector beam;
   input and output diverter mirrors for reflecting light at a constant angle, the input diverter mirror receiving the collimated input beam from the input transfer optics, and the output diverter mirror transmitting the collimated output beam of light to the output transfer optics, the diverter mirrors joined together and movable linearly along the beam axis;
   opposed input and output parabolic mirrors, the input parabolic mirror receiving a constant angle input beam from the input diverter mirror and focussing the light on the sample at a projection angle, the output parabolic mirror detecting the reflected light from the sample at a detection angle and transmitting a constant angle output beam to the output diverter mirror; and
   the input and output diverter mirrors being positioned so that the angle of projection equals the angle of detection throughout a linear range of positions of the diverter mirrors along the beam axis, the projection angle and the detection angle changing as the diverter mirrors linearly move.

2. The specular reflection system of claim 1 wherein the input and output parabolic mirrors have identical axes of symmetry and the motion of the joined diverter mirrors is perpendicular to the axes of symmetry.

3. The specular reflection system of claim 1 wherein the input and output parabolic mirrors have axes of symmetry which are angled relative to each other so as to permit light to be directed at the sample at very high angles of incidence.

4. The specular reflection system of claim 1 including an attenuated total reflectance crystal having opposed first and second transparent ends wherein the input parabolic mirror focuses a constant angle input beam from the input diverter mirror on the first end of the attenuated total reflectance crystal prism and the output parabolic mirror detects the light transmitted by the second end of the attenuated total reflectance crystal.

5. An accessory for insertion in the sample chamber of a spectroscopic instrument comprising
   input transfer optics for receiving a source beam from the instrument and directing a collimated input beam along a beam axis;
   output transfer optics for receiving a collimated output beam directed along the beam axis to produce a detector beam directed to the instrument;
   input and output diverter mirrors for reflecting light at a constant angle, the input diverter mirror receiving the collimated input beam from the input transfer optics, and the output diverter mirror transmitting the collimated output beam of light to the output transfer optics, the diverter mirrors linearly movable along the beam axis;
   a sample located at the exterior of the accessory;
   opposed input and output parabolic mirrors, the input parabolic mirror receiving a constant angle input beam from the input diverter mirror and directing the light on the sample at a projection angle, the output parabolic mirror receiving the reflected light from the sample at a detection angle and transmitting a constant angle output beam to the output diverter mirror; and the input and output diverter mirrors being joined so that the angle of projection equals the angle of detection throughout a range of positions of the diverter mirrors along the beam axis.

6. The accessory of claim 5 wherein the input and output parabolic mirrors have the same axis of symmetry and wherein the input and output diverter mirrors move perpendicular to that axis of symmetry.

7. The accessory of claim 5 wherein the axes of symmetry of the input and output parabolic mirrors are angled with respect to each other so that light can be directed at the sample at high angles of incidence.

8. The accessory of claim 5 wherein there is further an iris in the input transfer optics so that the amount of light incident on the sample can be limited to avoid directing light over a larger than desired area at the sample.

9. The accessory of claim 5 wherein the input transfer optics creates a collimated beam by directing converging input light beam onto a parabolic mirror.

10. The accessory of claim 5 wherein the output transfer optics creates a diverging light beam out of the accessory by directing the output collimated light beam at a parabolic output mirror.

11. An accessory for insertion in the sample chamber of a spectroscopic instrument comprising:
   input transfer optics for receiving a source beam from the instrument and directing a collimated input beam along a beam axis;
   output transfer optics for receiving a collimated output beam directed along the beam axis to produce a detector beam directed to the instrument;
   input and output diverter mirrors for reflecting light at a constant angle, the input diverter mirror receiving the collimated input beam from the input transfer optics, and the output diverter mirror transmitting the collimated output beam of light to the output transfer optics, the diverter mirrors movable along the beam axis;

a sample located at the exterior of the accessory;

opposed input and output parabolic mirrors, the input parabolic mirror receiving a constant angle input beam from the input diverter mirror and directing the light on the sample at a projection angle, the output parabolic mirror receiving the reflected light from the sample at a detection angle and transmitting a constant angle output beam to the output diverter mirror; and the input and output diverter mirrors being joined so that the angle of projection equals the angle of detection throughout a range of positions of the diverter mirrors along the beam axis; and wherein the input transfer optics include iris so that the amount of light incident on the sample can be limited to avoid directing light over a larger than desired area at the sample.

* * * * *